(12) United States Patent
Bramucci et al.

(10) Patent No.: US 6,187,569 B1
(45) Date of Patent: Feb. 13, 2001

(54) MICROBIAL PRODUCTION OF TEREPHTHALIC ACID AND ISOPHTHALIC ACID

(75) Inventors: Michael G. Bramucci, Folsom, PA (US); Carol M. McCutchen, Dickson, TN (US); Vasantha Nagarajan; Stuart M. Thomas, both of Wilmington, DE (US)

(73) Assignee: E. I. du Pont de Nemours and Company, Wilmington, DE (US)

( * ) Notice: Under 35 U.S.C. 154(b), the term of this patent shall be extended for 0 days.

(21) Appl. No.: 09/342,579

(22) Filed: Jun. 29, 1999

Related U.S. Application Data

(60) Provisional application No. 60/091,645, filed on Jul. 2, 1998.

(51) Int. Cl.[7] .................................. C12P 1/00; C12P 7/40; C12P 7/44; C12P 7/42; C12P 7/02
(52) U.S. Cl. ..................... 435/136; 435/41; 435/142; 435/146; 435/155; 435/156; 435/170
(58) Field of Search ..................... 435/136, 142, 435/146, 155, 156, 170, 41

(56) References Cited

FOREIGN PATENT DOCUMENTS

| 74013990 | * | 4/1974 | (JP) . |
| 9023891 | | 1/1997 | (JP) . |
| 419509 | | 3/1974 | (SU) . |

OTHER PUBLICATIONS

Worsey et al. 1978. Regulation of the Degradative Pathway Enzymes Coded for by the TOL Plasmid (pWWO) from Pseudomonas Putida mt–2. Journal of Bacteriology, 134: p.757764, Jun. 1978.*
A. Massol–Deya, et al. 1997. Succession and Convergence of Biofilm Communities in Fixed–Film Reactors Treating Hydrocarbons in Groundwater. Applied and Environmental Microbiology. 63: p. 270–276, Jan. 1997.*
Molecular Biology of Pseudomonads, Edited by T. Nakazawa et al., ASM Press, Washington, DC, Chapter 3, Pseudomonas Genetics and Taxonomy by Bruce W. Holloway, p. 22–31, 1996.*
Dagley et al., Microbial Physiol. 6:1–46 (1971).
Assinder et al., Adv. Microbial Physiol. 31: 1–69 (1990).
Burlage et al., Appl. Environ Microbiol 55: 1323–1328 (1989).
Junker et al., J. Bacteriol. 179: 919–927 (1997).
Junker et al., Microbiology 142: 2419–2427 (1996).

* cited by examiner

*Primary Examiner*—Leon B. Lankford, Jr.
*Assistant Examiner*—Michele C. Flood

(57) ABSTRACT

This invention relates to a biocatalytic process to produce terephthalic acid and isophthalic acid from p-xylene and m-xylene, respectively. Terephthalic acid has been prepared by oxidizing p-xylene with bacteria belonging to the genus Burkholderia. Conversion of p-xylene into terephthalic acid is accomplished by a single bacterial strain that produces all of the requisite enzymes. In addition, this invention relates to the preparation of isophthalic acid from a mixture of m- and p-xylene.

5 Claims, 9 Drawing Sheets

SEQUENCE LISTING

<160> NUMBER OF SEQ ID NOS: 4

<210> SEQ ID NO 1
<211> LENGTH: 1451
<212> TYPE: DNA
<213> ORGANISM: Burkholderia sp.

<400> SEQUENCE: 1

```
tggaacgctg gcggcatgc cttacacatg caattcaaac ggcagcacgg gtgcttgcac      60
ctggtggcga ttggcgaacg ggtgattaat acatcggaat gtaccttgta gtgggggata    120
cctcggcaaa agccggatta ataccgcata cgctctgagg aggaaagcgg gggaccttcg    180
ggcctcgcgc tacaaaagca gccgatgtca aattacctat ttggtgggt aaaagctcac     240
caaggcgaca atctgtacct ggtctgagag gacaaccacc cacactggga ctgaaacacg    300
gcccaaactc ctacgggagg cagcagtggg gaattttgga caatgggcga aagcctgatc    360
caccaatgcc gcgtgtgtga aaaaggcctt cgggttgtaa agcacttttg tccggaaaga    420
aatcctctgg gttaatacct cgggggggatg acggtaccgg aaaaataagc accggctaac    480
tacttgccac agccgcggta atacttaggg tgcaagcgtt aatcggaatt actgggcgta    540
aagcgtgcgc aggcggtttt gtaagacgga tgtgaaatcc ccgggcttaa cctgggaact    600
gcattcgtga ctgcaaggct agagtatggc agaggggggt agaattccac gtgtagcagt    660
gaaatgcgta gagatgtgga ggaataccga tggcgaaggc agcccctgg gccaatactg    720
acgctcatgc acgaaagcgt ggggagcaaa caggattaga taccctggta gtccacgccc    780
taaacgatgt caactagttg ttggggattc atttccttag taacgaagct aacgcgtgaa    840
gttgaccgcc tggggagtac ggtcgcaaga ttaaaactca aaggaattga cggggacccg    900
cacaagcggt ggatgatgtg gattaattcg atgcaacgcg aaaaacctta cctacccttg    960
acatgtacgg aatcttgctg agaggtgaga gtgctcgaaa gagaaccgta acacaggtgc   1020
tgcatggctg tcgtcagctc gtgtcgtgag atgttgggtt aagtcccgca acgagcgcaa   1080
cccttgtcct tagttgctac gcaagagcac tctaaggaga ctgccggtga caaaccggag   1140
gaaggtgggg atgacgtcaa gtcctcatgg cccttatggg tagggcttca cacgtcatac   1200
aatggtcggt acagagggct gccaaaccgc gaggtggagc taacccccaga aaaccgatcg   1260
tagtccggat cgcagtctgc aactcgactg cgtgaagctg gaatcgctag taatcgcgga   1320
```

-continued

```
tcagcatgtc gcggtgaata cgttcccggg tcttgtacac accgcccgtc acaccatggg    1380
agtgggtttt gccagaagta ggtagcctaa ccgtaaggag ggcgcttacc acggcaggat    1440
catgactggg g                                                         1451
```

```
<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence:  HK12
      primer

<400> SEQUENCE: 2
gagtttgatc ctggctcag                                                   19

<210> SEQ ID NO 3
<211> LENGTH: 16
<212> TYPE: DNA
<213> ORGANISM: Artificial Sequence
<220> FEATURE:
<223> OTHER INFORMATION: Description of Artificial Sequence:  HK13
      primer

<400> SEQUENCE: 3
taccttgtta cgactt                                                      16

<210> SEQ ID NO 4
<211> LENGTH: 17
<212> TYPE: DNA
<213> ORGANISM: Artificial Sequence
<220> FEATURE:
<223> OTHER INFORMATION: Description of Artificial Sequence:  HK14
       primer
<220> FEATURE:
<221> NAME/KEY: misc_feature
<222> LOCATION: (11)
<223> OTHER INFORMATION: Y = C or T
<220> FEATURE:
<221> NAME/KEY: misc_feature
<222> LOCATION: (12)
<223> OTHER INFORMATION: M = A or C

<400> SEQUENCE: 4
gtgccagcag ymgcggt                                                     17
```

MICROBIAL PRODUCTION OF TEREPHTHALIC ACID AND ISOPHTHALIC ACID

This application claims the benefit of U.S. Provisional Application No. 60/091,645, filed Jul. 2, 1998.

FIELD OF INVENTION

This invention pertains to methods for the production of terephthalic acid and isophthalic acid by bacteria.

BACKGROUND

Terephthalic acid and isophthalic acid are two monomers having utility in the production of polyesters which are commercially required in large quantities for fibers, films, paints, adhesives and beverage containers. Isophthalic acid is also used in condensation reactions with diamines to form polyamides. Polyesters and polyamides are two extremely important classes of commercial polymers.

A variety of chemical routes to terephthalic acid and isophthalic acid are known. The most notable commercial process to prepare terephthalic acid involves the liquid-phase oxidation of p-xylene. The Amoco process involves oxidizing p-xylene with a molecular oxygen-containing gas in the liquid phase in a lower aliphatic monocarboxylic acid solvent in the presence of a heavy metal catalyst and a bromine compound to from terephthalic acid directly (U.S. Pat. No. 2,833,816). More specifically, the reaction is catalyzed by Co and Mn in 95% acetic acid with a mixture of $NH_4Br$ and tetrabromoethane as cocatalysts. The oxidation is carried out under severe conditions of high temperatures (109–205° C.) and pressures (15–30 bar). Hence, the rate of reaction is high and the yield of terephthalic acid based on p-xylene is as high as 95% or more. However, the reaction apparatus becomes heavily corroded owing mainly to the use of the bromine compound and the monocarboxylic acid solvent. Thus, ordinary stainless steel can not be used to build the reaction apparatus, and expensive materials such as Hastelloy or titanium are required. In addition, because the acid solvent is used in large quantity and the oxidation conditions are severe, combustion of the solvent itself can not be avoided, and its loss is not negligible. The Amoco process has also been shown to oxidize m-xylene to isophthalic acid. Although it is possible to oxidize xylenes by these methods, they are expensive and generate waste streams containing environmental pollutants.

Biological oxidation of methyl groups on aromatic rings, such as toluene and isomers of xylene, is well known (Dagley et al., *Adv. Microbial Physiol.* 6:1–46 (1971)). For example, bacteria that have the xyl genes for the Tol pathway sequentially oxidize the methyl group on toluene to afford benzyl alcohol, benzaldehyde and ultimately benzoic acid. The xyl genes located on the well characterized Tol plasmid pWWO have been sequenced (Assinder et al., *Adv. Microbial Physiol.* 31:1–69 (1990); Burlage et al., *Appl. Environ. Microbiol.* 55:1323–1328 (1989)). The xyl genes are organized into two operons. The upper pathway operon encodes the enzymes required for oxidation of toluene to benzoic acid. The lower pathway operon encodes enzymes that convert benzoic acid into intermediates of the tricarboxylic acid (TCA) cycle.

In addition to toluene, m-xylene and p-xylene are substrates of the Tol pathway (JP 9023891). The upper pathway enzymes catalyze oxidation of one methyl group on m-xylene and p-xylene to produce the corresponding methylbenzyl alcohol, methylbenzaldehyde and methylbenzoic acid. Although many bacteria utilize m-xylene and/or p-xylene as sources of carbon and energy for growth, essentially all of the known examples oxidize m-xylene or p-xylene to methylbenzoic acid (i.e., m-toluic acid or p-toluic acid) and then convert the methylbenzoic acid to methylcatechol. Bacteria with the Tol pathway have not been shown to produce isophthalic acid or terephthalic acid as intermediates when p- and m-xylene are used as substrates. However, certain bacteria are known to oxidize the methyl group of methylbenzoic acid when this compound is degraded to provide carbon and energy for growth. For example, *Comamonas testosteroni* strain T-2 oxidizes p-methylbenzoic acid (p-toluic acid) to terephthalic acid (Junker et al., *J. Bacteriol.* 179:919–927 (1997); Junker et al., *Microbiology* 142:2419–2427 (1996)). It is important to note that although this strain degrades methylated aromatics such as p-toluenesulfonic acid, it displays no activity against toluene or p-xylene.

In general, biological processes for production of chemicals are desirable for several reasons. One advantage is that the enzymes that catalyze biological reactions have substrate specificity. Accordingly, it is sometimes possible to use a starting material that contains a complex mixture of compounds to produce a specific chiral or structural isomer via a biological process. Another advantage is that biological processes are commonly perceived as being less harmful to the environment than chemical manufacturing processes. These advantages, among others, make it desirable to use p-xylene or m-xylene as the starting materials for manufacture of terephthalic acid or isophthalic acid, respectively, by means of a bioprocess.

SU 419509 claims a method for the cooxidative production of terephthalic acid by the microbiological transformation of p-xylene using an active culture from the genus Nocardia, which carries out the direct oxidation of p-xylene to terephthalic acid. The method is described as a cooxidative process that involves providing the bacteria with hexadecane and p-xylene. Since this is a cooxidative process, the hexadecane is required to induce synthesis of the appropriate oxidative enzymes.

Finally, JP 9023891 claims a method for the production of aromatic carboxylic acids by oxidation of various aromatic compounds by Mycobacterium sp. strain NS12523 and similar bacteria belonging to the genus Mycobacterium. Terephthalic acid and isophthalic acid are two of the aromatic carboxylic acids claimed to be formed by the described process. However, there was no demonstration that the claimed Mycobacterium strains could actually produce terephthalic acid or isophthalic acid. When p-xylene was used as a substrate, only p-toluic acid was isolated as the product. If p-toluic acid could be used as a substrate, as was claimed, it would be reasonable to expect terephthalic acid to be isolated with or as the final product.

A need exists for environmentally friendly, safe and economical methods to produce compounds of commercial interest. A method that has broad applicability for the production of terephthalic acid and isophthalic acid would have great commercial value. To the best of applicants' knowledge, there is no account of any bacteria that can oxidize both methyl groups of p-xylene to form terephthalic acid in the absence of a cooxidized compound. Furthermore, no such method involving the biological oxidation of both methyl groups of p- and m-xylene by a single organism was previously known.

SUMMARY OF THE INVENTION

The present invention provides a TPA producing microorganism isolated by the process comprising: (i) culturing a sample suspected of containing a TPA producing microorganism in a suitable growth medium containing at least one aromatic organic substrate selected from the group consisting of p-xylene, p-toluic acid, and terephthalic acid; (ii) selecting those microorganisms which are able to use every substrate selected individually from the group consisting of p-xylene, p-toluic acid, and terephthalic acid as a sole carbon source; (iii) contacting the microorganisms selected in step (ii) with p-xylene to form a reaction medium; and (iv) monitoring the reaction medium over time for the presence of terephthalic acid, whereby the production of terephthalic acid indicates the presence of a TPA producing microorganism. Preferred TPA producing microorganisms are bacteria which comprising the genes encoding the TPA biosynthetic pathway and are members of Proteobacteria.

The invention further provides a process for the isolation of a TPA producing microorganism comprising: (i) culturing a sample suspected of containing a TPA producing microorganism in a suitable growth medium containing at least one aromatic organic substrate selected from the group consisting of p-xylene, p-toluic acid, and terephthalic acid; (ii) selecting those microorganisms which are able to use every substrate selected individually from the group consisting of p-xylene, p-toluic acid, and terephthalic acid as a sole carbon source; (iii) contacting the microorganisms selected in step (ii) with p-xylene to form a reaction medium; and (iv) monitoring the reaction medium over time for the presence of terephthalic acid, whereby the production of terephthalic acid indicates the presence of a TPA producing microorganism.

In an alternate embodiment the invention provides a process for the production of terephthalic acid comprising: (i) contacting an isolated TPA producing microorganism with an aromatic organic substrate whereby terephthalic acid accumulates; and (ii) optionally recovering the terephthalic acid. The process for terephthalic acid production may optionally use any one of the aromatic organic substrates p-xylene, 4-methylbenzyl alcohol, p-tolualdehyde, p-toluic acid, 4-carboxybenzyl alcohol, and 4-carboxybenzaldehyde.

The invention further provides a process for the production of various intermediates in the synthesis of TPA such as 4-carboxybenzyl alcohol and 4-carboxybenzaldehyde.

The invention additionally provides a method for the production of isophthalic acid comprising: (i) contacting an isolated TPA producing microorganism with an aromatic organic substrate and at least one suitable induction compound whereby isophthalic acid accumulates; and (ii) optionally recovering the isophthalic acid. The process for isophthalic acid production may optionally use any one of the aromatic organic substrates of m-xylene, 3-methylbenzyl alcohol, m-tolualdehyde, m-toluic acid, 3-carboxybenzyl alcohol, 3-carboxybenzaldehyde and isophthalic acid.

In another embodiment the invention provides a process for the production of terephthalic acid comprising: (i) contacting a mixed population of microorganisms comprising the genes encoding the TPA biosynthetic pathway, with an aromatic organic substrate whereby terephthalic acid accumulates; and (ii) optionally recovering the terephthalic acid.

TABLE DESCRIPTIONS, SEQUENCE DESCRIPTIONS AND BIOLOGICAL DEPOSITS

Figure 1:
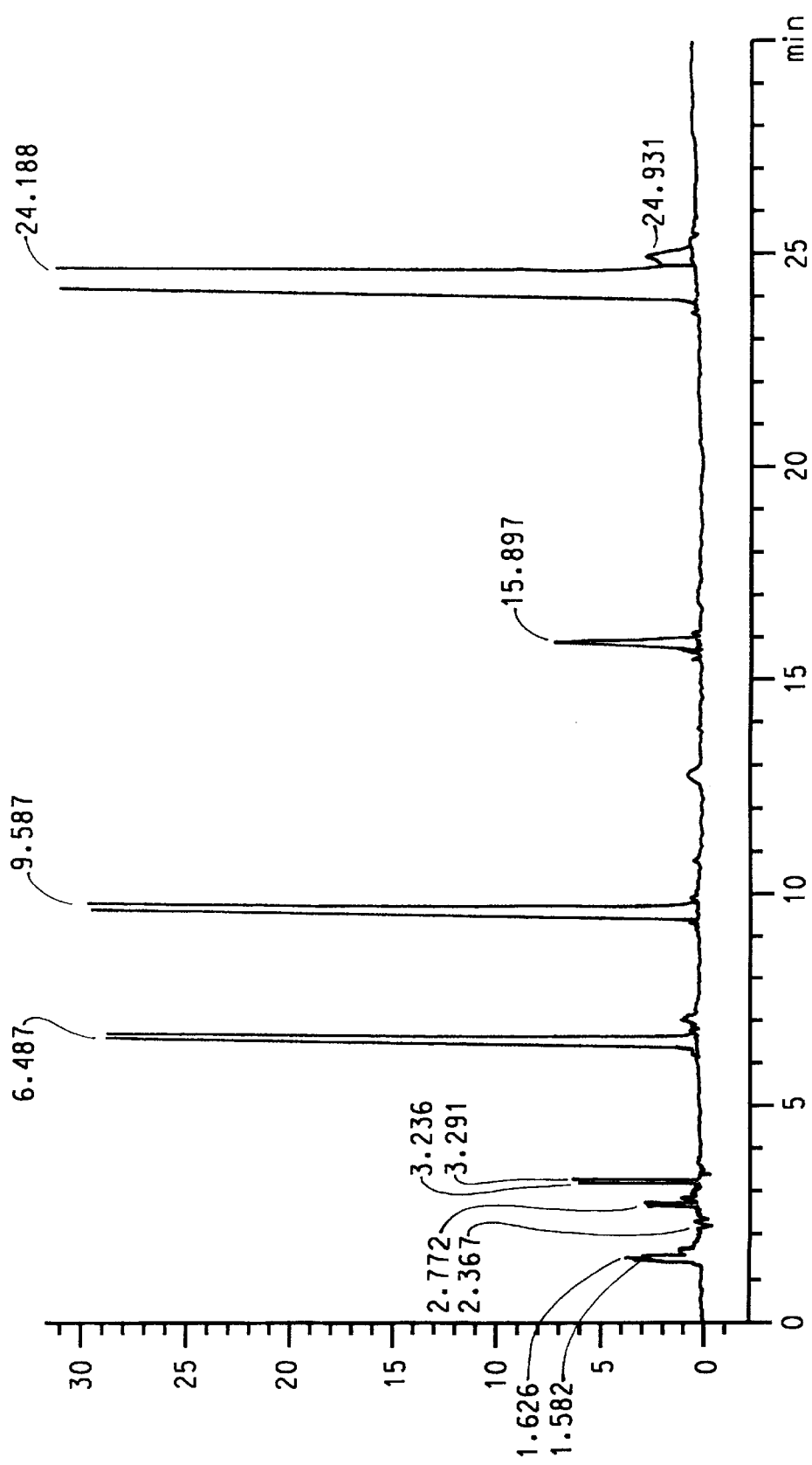
FIG. 1 is a HPLC analysis of a biotransformation of p-xylene by Burkholderia.
Figure 2A:
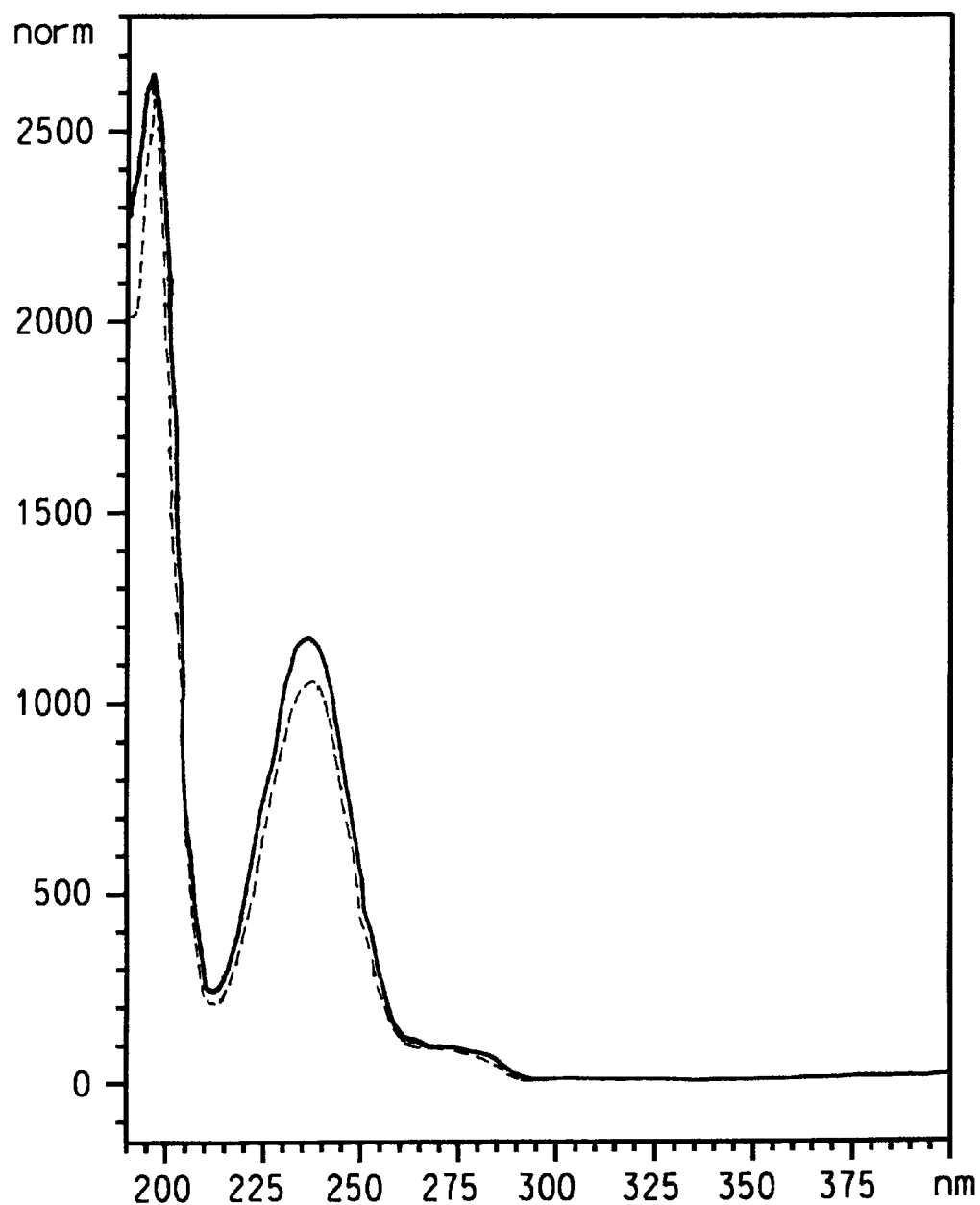
FIG. 2A is a plot of an UV absorbance spectrum of authentic 4-carboxybenzyl alcohol.
Figure 2B:
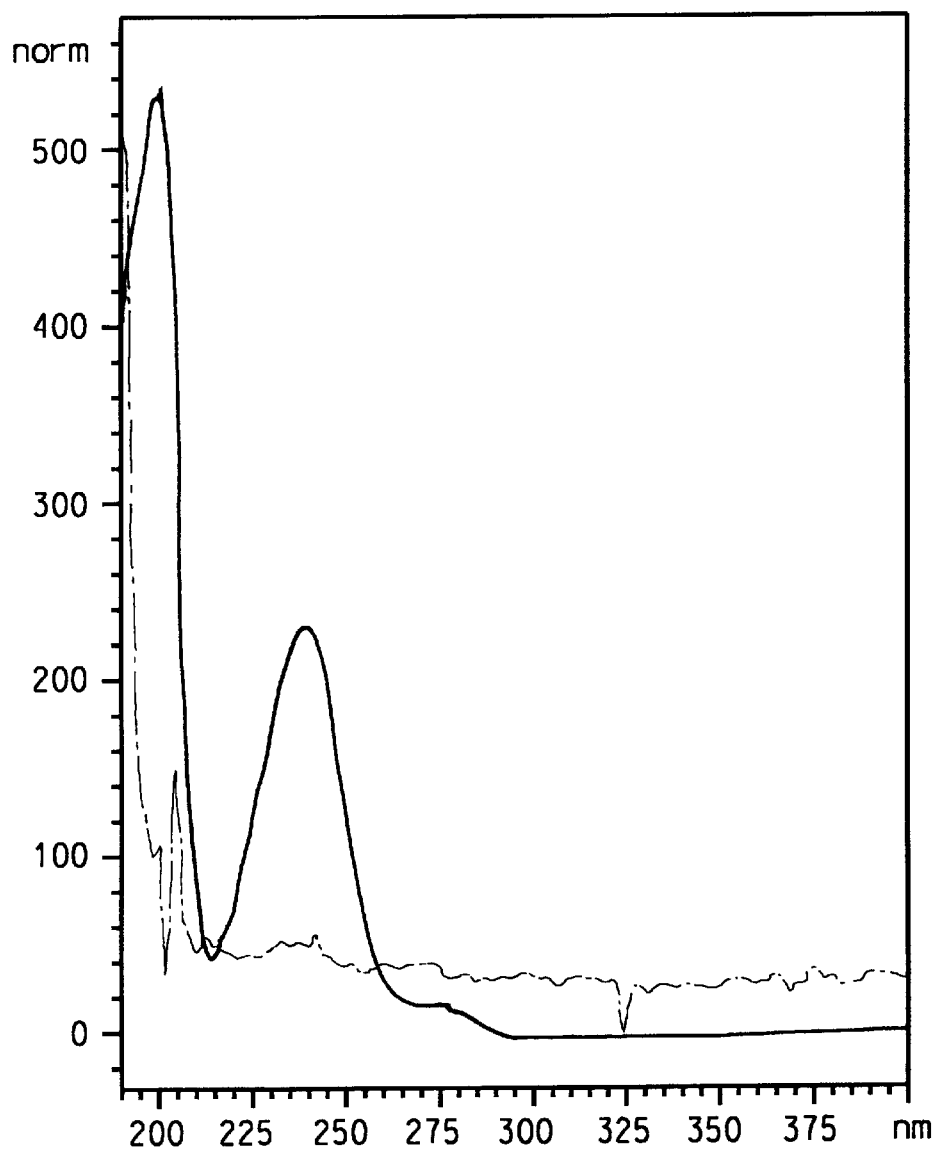
FIG. 2B is a plot of an UV absorbance spectrum of presumptive 4-carboxybenzyl alcohol.
Figure 3A:
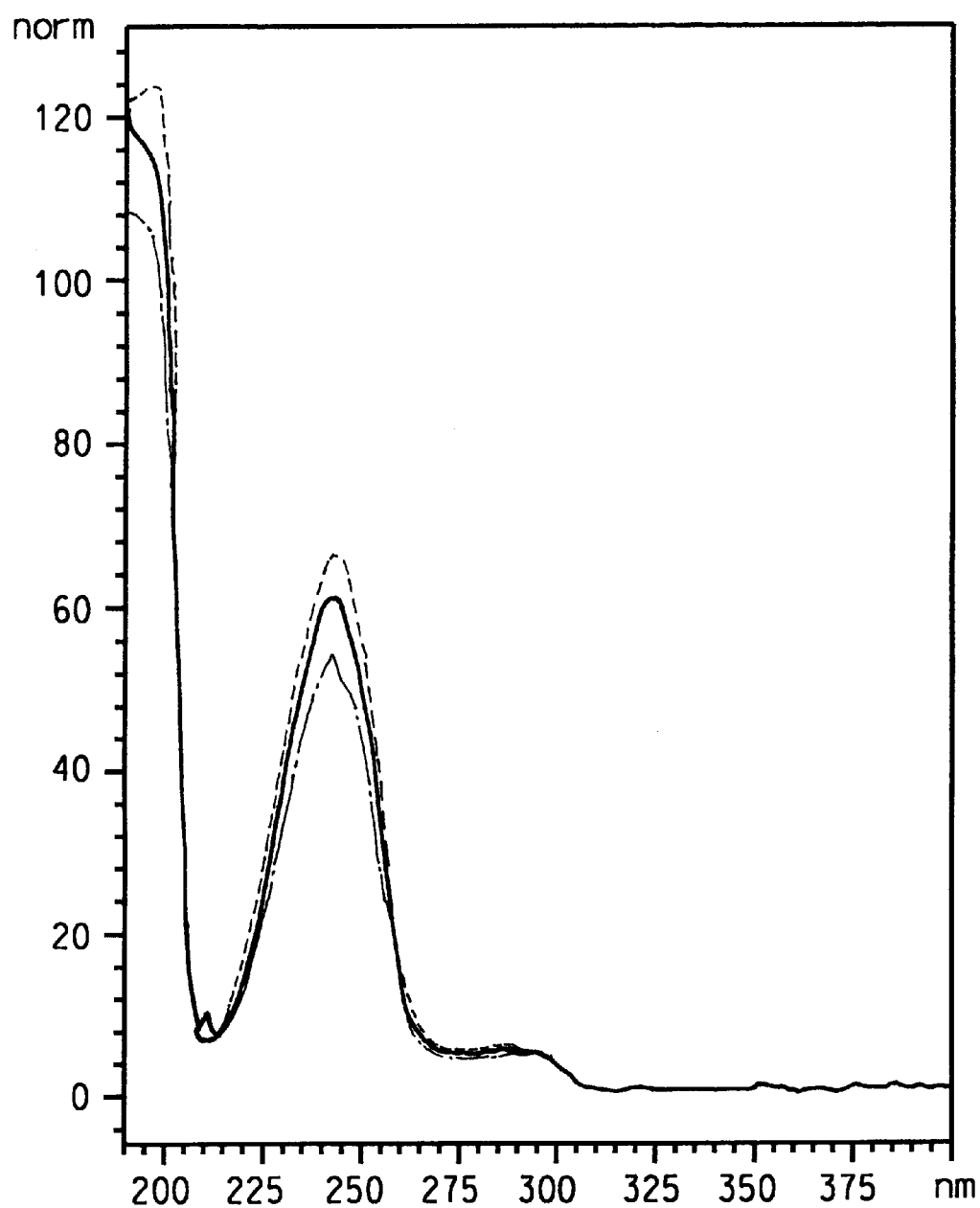
FIG. 3A is a plot of an UV absorbance spectrum of authentic terephthalic acid.
Figure 3B:
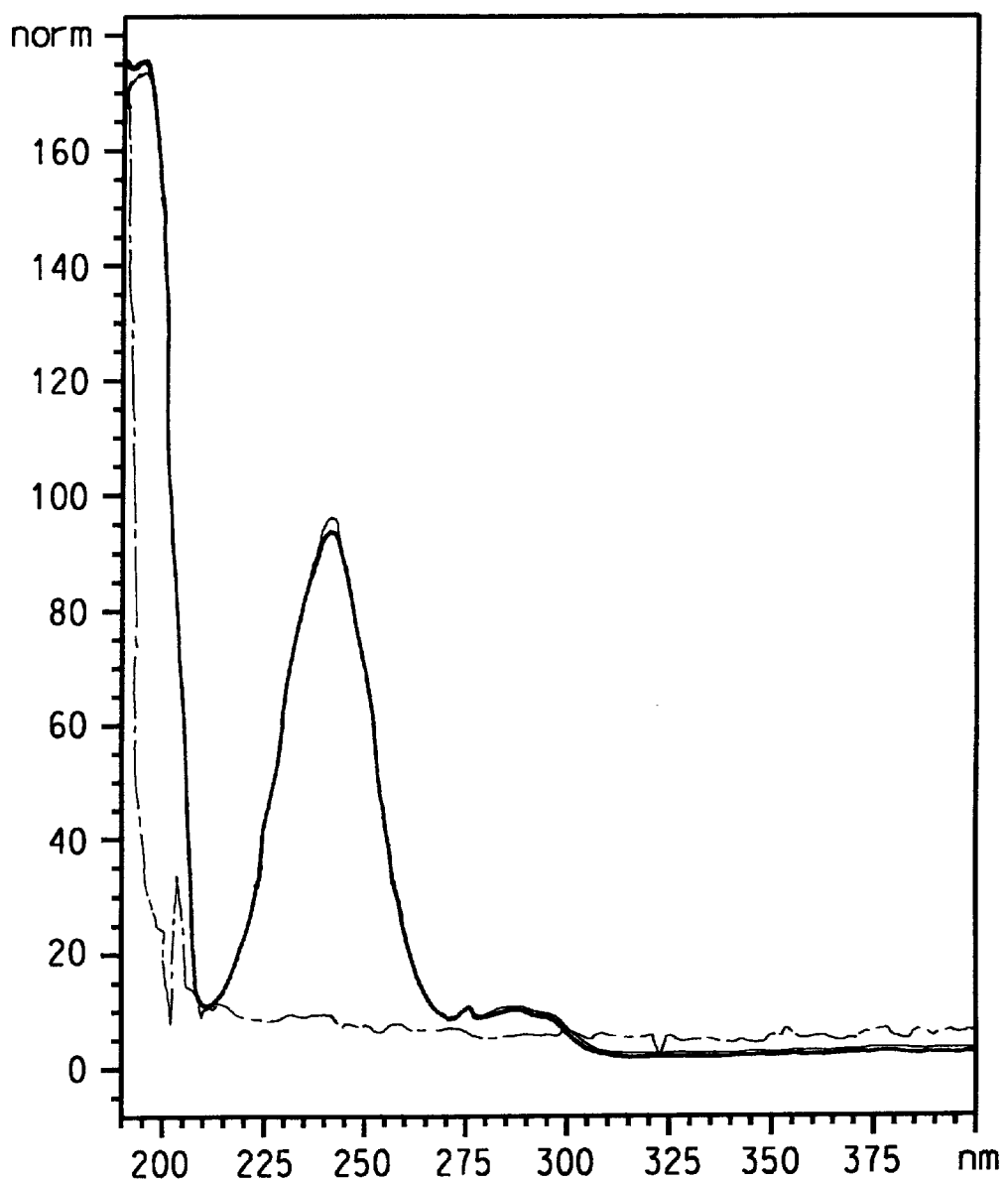
FIG. 3B is a plot of an UV absorbance spectrum of presumptive terephthalic acid.
Figure 4A:
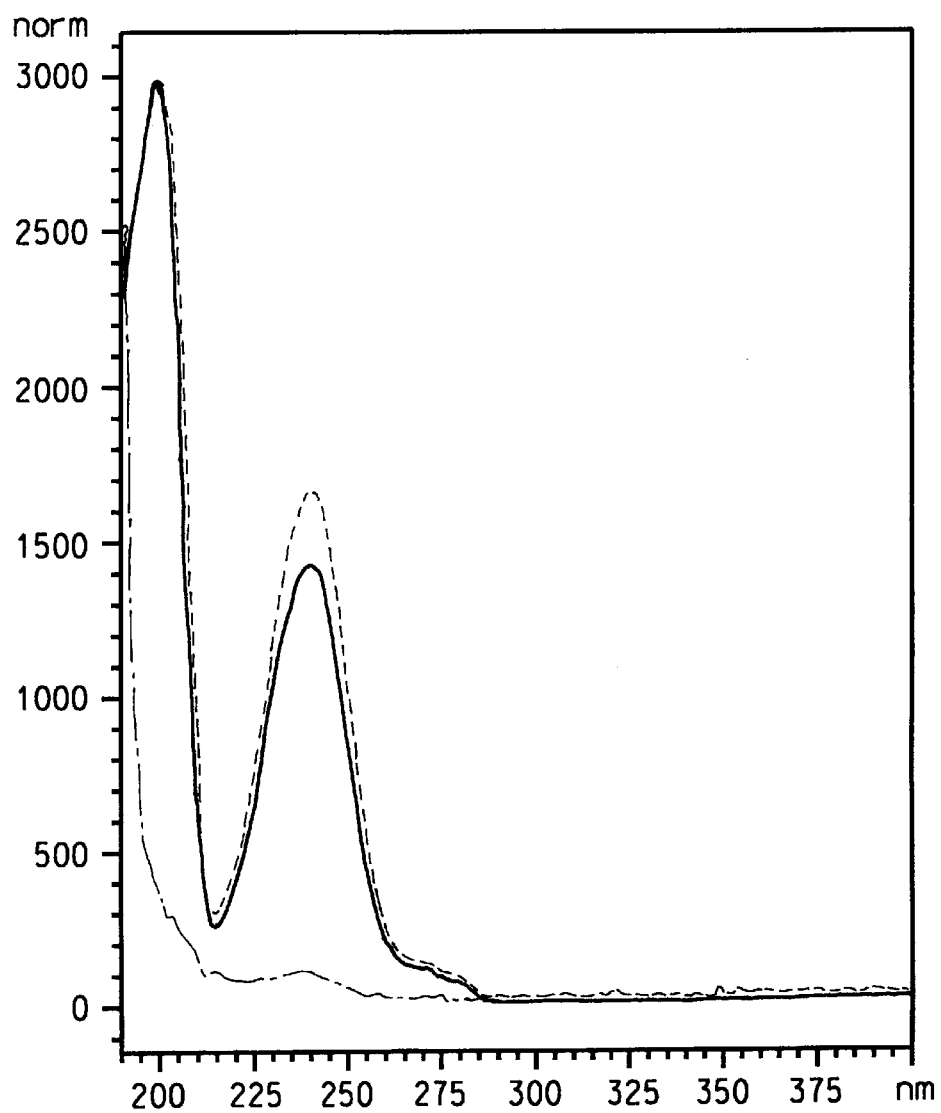
FIG. 4A is a plot of an UV absorbance spectrum of authentic p-toluic acid.
Figure 4B:
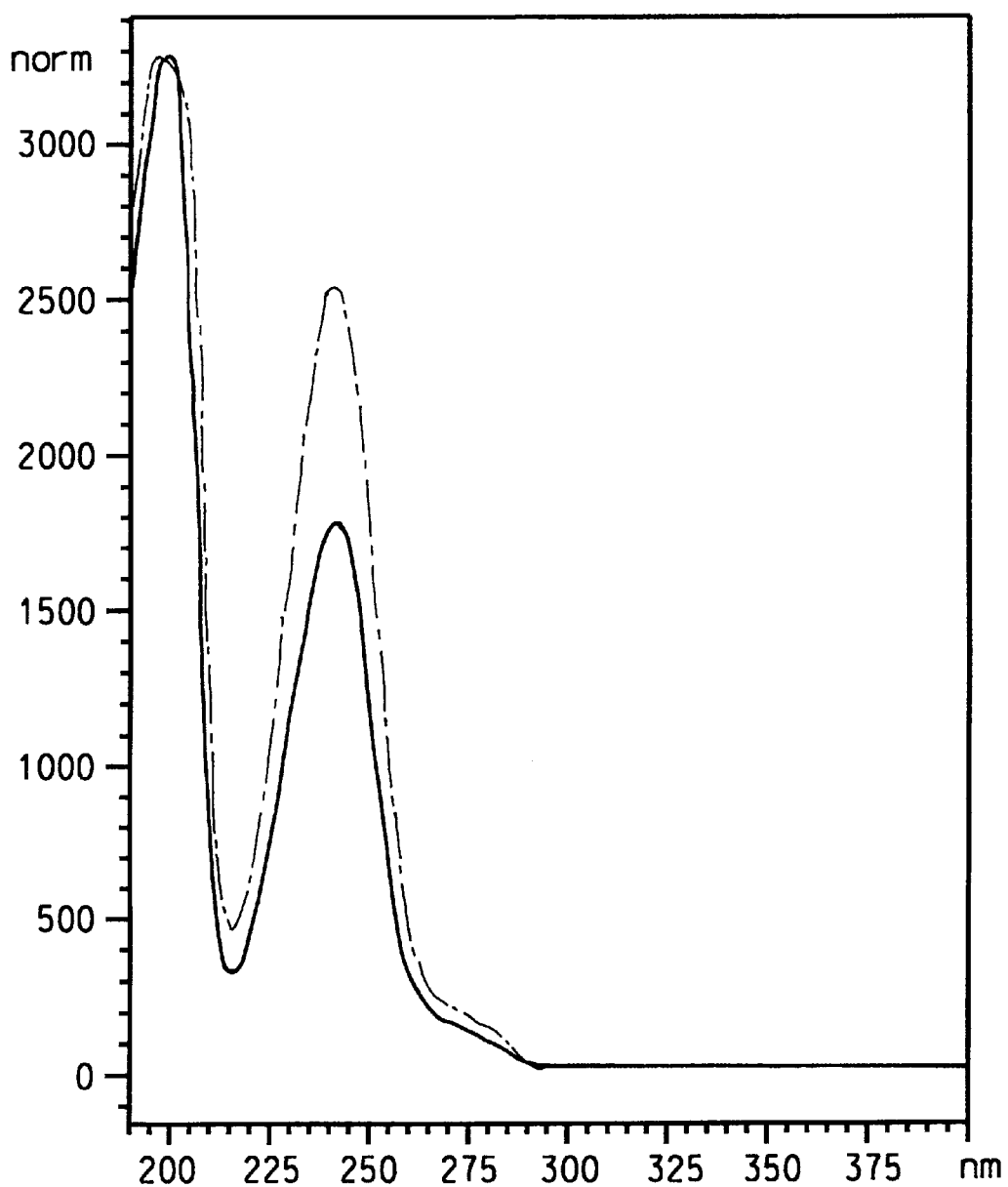
FIG. 4B is a plot of an UV absorbance spectrum of presumptive p-toluic acid.

Table 1 contains a summary of carbon source utilization.

Table 2 contains a comparison of 16s rRNA genes.

Table 3 details the production of p-toluic acid and terephthalic acid from p-xylene by Burkholderia strain IR3.

Table 4 details the production of p-toluic acid and terephthalic acid after growth in LB medium.

Table 5 details the production of m-toluic acid and isophthalic acid from m-xylene by Burkholderia strain IR3.

Table 6 details the production of terephthalic acid from p-xylene in mixed cultures of ATCC 33015 and DSM 6577.

The invention can be more fully understood from the following detailed description and the accompanying sequence descriptions which form a part of this application.

The following sequence descriptions and sequences listings attached hereto comply with the rules governing nucleotide and/or amino acid sequence disclosures in patent applications as set forth in 37 C.F.R. §1.821–1.825. The Sequence Descriptions contain the one letter code for nucleotide sequence characters and the three letter codes for amino acids as defined in conformity with the IUPAC-IYUB standards described in *Nucleic Acids Research* 13:3021–3030 (1985) and in the *Biochemical Journal* 219 (No. 2):345–373 (1984) which are herein incorporated by reference. The symbols and format used for nucleotide and amino acid sequence data comply with the rules set forth in 37 C.F.R. §1.822.

SEQ ID NO:1 is the nucleotide sequence of a 16s rRNA gene from isolate IR3.

SEQ ID NO:2 is the HK12 primer.

SEQ ID NO:3 is the HK13 primer.

SEQ ID NO:4 is the HK14 primer.

Applicants have made the following biological deposits under the terms of the Budapest Treaty on the International Recognition of the Deposit of Microorganisms for the Purposes of Patent Procedure:

| Depositor Identification Reference | International Depository Designation | Date of Deposit |
|---|---|---|
| Burkholderia sp. IR3 | ATCC 202150 | 2 July 1998 |
| Burkholderia sp. IR10 | ATCC 202151 | 2 July 1998 |

DETAILED DESCRIPTION OF THE INVENTION

The present invention is a process for the production terephthalic acid (TPA) involving the bioconversion of p-xylene to TPA using a single TPA producing microorganism. The TPA producing organism comprises the genes encoding enzymes involved in the enzymatic conversion of p-xylene to TPA as follows: p-xylene is acted upon by xylene monooygenase to form 4-methylbenzyl alcohol, which is acted upon by methylbenzyl alcohol dehydrogenase to form p-tolualdehyde, which is acted upon by tolualdehyde dehydrogenase to form p-toluic acid, which is acted upon by toluate methyl monooxygenase to form 4-carboxybenzyl alcohol, which is acted upon by carboxybenzyl alcohol methyl dehydrogenase to form 4-carboxybenzaldehyde, which is acted upon by caboxybenzaldehyde methyl dehydrogenase to form terephthalic acid. This enzymatic pathway is referred to herein as the TPA biosynthetic pathway.

In another embodiment of the invention, m-xylene is enzymatically transformed to isophthalate by a TPA producing microorganism comprising the TPA biosynthetic pathway. The enzymes involved in the pathway are the same, however the intermediates are all meta substituted as follows: m-xylene, to 3-methylbenzyl alcohol, to m-tolualdehyde, to m-toluic acid, to 3-carboxybenzyl alcohol, to 3-carboxybenzaldehyde and finally to isophthalic acid.

The TPA producing microorganism of the present invention is isolated from activate sludge in the presence of several different aromatic organic substrates. Those microorganisms having an ability to grow on these substrates are then screened for their ability to bioconvert either p-xylene or m-xlyene to terephthalate or isophthalate respectively.

It is another aspect of the invention, a mixture of microorganisms, collectively containing the genes encoding the TPA biosynthetic pathway may be cultured as a mixed popultation for the bioconversion p-xylene or m-xylene to their respective products.

The present invention is useful for the biological production of terephthalic acid and isophthalic acid which have utility in the production of polyesters needed in fibers, films, paints, adhesives and beverage containers. The present invention advances the art of the synthesis of terephthalic acid and isophthalic acid as biological processes are more cost effective and produce fewer environmentally harmful waste products.

In this disclosure, a number of terms and abbreviations are used. The following definitions are provided.

"Terephthalic acid" is abbreviated TPA.
"Isophthalic acid" is abbreviated IPA.
"Dihydroxybenzoic acid" is abbreviated as DHBA.
"Trimalinic acid" is abbreviated as TMA.
"Phthalic acid" is abbreviated as PA.
"4-Carboxybenzyl alcohol" is abbreviated at 4-CBAL.
"4-Carboxybenzaldehyde" is abbreviated at 4-CBA.
"Benzoic acid" is abbreviated at BA.
"p-Toluic acid" is abbreviated as PTA.
"p-Tolualdehyde" is abbreviated as PTL.
"Ethylenediaminetetraacetic acid" is abbreviated as EDTA.
"Open reading frame" is abbreviated ORF.
"Polymerase chain reaction" is abbreviated PCR.

As used herein, "ATCC" refers to the American Type Culture Collection International Depository located at 10801 University Boulevard, Manassaa, Va. 20110-2209, U.S.A. The "ATCC No." is the accession number to cultures on deposit with the ATCC.

The term "TPA biosynthetic pathway" refers to the seqeunce of enzymatic steps that will convert either p-xylene to terephthalic acid or m-xylene to isophthalic acid and consists of enzymes in the following seqeunce: 1—xylene monooygenase→2—methylbenzyl alcohol dehydrogenase→3—tolualdehyde dehydrogenase→4—toluate methyl monooxygenase→5—carboxybenzyl alcohol methyl dehydrogenase→6—caboxybenzaldehyde methyl dehydrogenase→7, where the numbers 1–7 refer to the compounds to be catalyzed.

The term "TPA producing microorganism" refers to any microorganism which converts p-xylene to TPA or m-xylene to isophthalate and which also comprises the enzymes of the TPA biosynthetic pathway.

The term "suitable induction compound" refers to any compound which, when co-fermented with a process starting material, facilities the bio-conversion of that starting material. Within the context of the present invention a suitable induction compound for the bio-conversion of m-xylene to isophthalate is p-xylene.

The terms "bio-transformation" and "bio-conversion" will be used interchangeably and will refer to the process of enzymatic conversion of a compound to another form or compound. The process of bio-conversion or bio-transformation is typically carried out by a bio-catalyst.

As used herein the term "bio-catalyst" refers to a microorganism which contains an enzyme or enzymes capable of bio-conversion of a specific compound or compounds.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991). Preferred methods to determine identity are designed to give the largest match between the sequences tested. Methods to determine identity and similarity are codified in publicly available computer programs. Preferred computer program methods to determine identity and similarity between two sequences include, but are not limited to, the GCG Pileup program found in the GCG program package, using the Needleman and Wunsch algorithm with their standard default values of gap creation penalty=12 and gap extension penalty=4 (Devereux et al., *Nucleic Acids Res.* 12:387–395 (1984)), BLASTP, BLASTN, and FASTA (Pearson et al., *Proc. Natl. Acad. Sci. U.S.A.* 85:2444–2448 (1988). The BLAST X program is publicly available from NCBI and other sources (*BLAST Manual*, Altschul et al., Natl. Cent. Biotechnol. Inf., Natl. Library Med. (NCBI NLM) NIH, Bethesda, Md. 20894; Altschul et al., *J. Mol. Biol.* 215:403–410 (1990)). Another preferred method to determine percent identity, is by the method of DNASTAR protein alignment protocol using the Jotun-Hein algorithm (Hein et al., *Methods Enzymol.* 183:626–645 (1990)). Default parameters for the Jotun-Hein method for alignments are: for multiple alignments, gap penalty=11, gap length penalty=3; for pairwise alignments ktuple=6. As an illustration, by a polynucleotide having a nucleotide sequence having at least, for example, 95% "identity" to a reference nucleotide sequence it is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

"Gene" refers to a nucleic acid fragment that expresses a specific RNA molecule (mRNA, rRNA, or tRNA) and which may, in addition, express a specific protein if the gene initially expresses a mRNA molecule. The gene includes regulatory sequences preceding (5' non-coding sequences) and following (3' non-coding sequences) the coding sequence.

Standard recombinant DNA and molecular cloning techniques used here are well known in the art and are described by Sambrook, J., Fritsch, E. F. and Maniatis, T., *Molecular Cloning: A Laboratory Manual*, Second Edition, Cold Spring Harbor Laboratory Press, Cold Spring Harbor, N.Y. (1989) (hereinafter "Maniatis"); and by Silhavy, T. J., Bennan, M. L. and Enquist, L. W., *Experiments with Gene Fusions*, Cold Spring Harbor Laboratory Cold Press Spring Harbor, N.Y. (1984); and by Ausubel, F. M. et al., *Current Protocols in Molecular Biology*, published by Greene Publishing Assoc. and Wiley-Interscience (1987).

Isolation of TPA Producing Microorganisms

The TPA producing microorganisms of the present invention may be isolated from a variety of sources. Suitable sources include industrial waste streams, soil from contaminated industrial sites and waste stream treatment facilities. The microorganisms of the present invention were isolated from activated sludge from a waste water treatment plant.

Samples suspected of containing TPA producing microorganisms may be enriched by incubation in a suitable growth medium in combination with at least one aromatic organic substrate. Suitable substrates may include those intermediates which are bio-transformed by the enzymes of the TPA biosynthetic pathway. Suitable aromatic organic substrates for use in the present invention include, but are not limited to p-xylene, 4-methylbenzyl alcohol, p-tolualdehyde, p-toluic acid, 4-carboxybenzyl alcohol, 4-carboxybenzaldehyde, terephthalic acid, m-xylene, 3-methylbenzyl alcohol, m-tolualdehyde, m-toluic acid, 3-carboxybenzyl alcohol, and 3-carboxybenzaldehyde, wherein p-xylene and p-toluic acid and terephthalic acid are preferred. It is preferred that the organism be able to use several different aromatic substrates as a sole carbon source. So for example, preferred microorganisms will be able to grow on p-xylene and terephthalic acid and one other intermediate. The preferred additional intermediate in the present invention was p-toluic acid.

Once microorganisms are identified as having the ability to use the aromatic substrates as the sole carbon/energy source they are then screened for the ability to bio-convert either p-xylene to TPA or m-xylene to IPA. This is accomplished by contacting a suitable amount of either p-xylene or m-xylene with the isolated organism in the presence of a growth medium and monitoring the culture for the appearance of the desired end product. Of 20 isolates identified in this manner, 3 had the ability to accomplish the desired bio-conversions.

Growth medium and techniques needed in the enrichment and screening of TPA producing microorganisms are well known in the art and examples may be found in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D,C. (1994)); or by Thomas D. Brock in *Biotechnology: A Textbook of Industrial Microbiology*, Second Edition, Sinauer Associates, Inc., Sunderland, Mass. (1989).

Characterization of TPA Producing Microorganisms

Microorganisms isolated according to the above procedure have several distinguishing characteristics. All contain the enzymes of the TPA biosynthetic pathway. All are included in the group Proteobacteria, of which Burkholderia, Alcaligenes, Pseudomonas, Sphingomonas, and Comamonas are examples. The Proteobacteria form a physiologically diverse group of microorganisms and represent five subdivisions ($\alpha$, $\beta$, $\gamma$, $\epsilon$, $\delta$) (Madigan, M. T., et al., Brock Biology of Microorganisms, 8th edition, Prentice Hall, UpperSaddle River, N.J. (1997)). All five subdivisions of the Proteobacteria contain microorganisms that use organic compounds as sources of carbon and energy. Although the specific microorganisms isolated were all of the genus Burkholderia($\beta$ subdivision) (i.e. IR3 [ATCC 202150] and IR10 [ATCC 202151]), it is contemplated that other members of the Proteobacteria isolated according to the above method will be suitable, e. g. Pseudomonas ($\gamma$ subdivision) and Sphingomonas ($\alpha$ subdivision), because genes for metabolism of p-xylene and other aromatic compounds are frequently located on plasmids and the plasmids are frequently capable of transferring between members of the Proteobacteria (Assinder and Williams, *Adv. Microb. Physiol.* 31:2–69 (1990); Springael, D. et al. *Microbiol* 142:3283–3293 (1996)).

Another characteristic of the present TPA producing organisms is that they appear to be genetically similar to members of the genus Burkholderia as determined by 16s rRNA comparison. 16s rRNA was isolated from the TPA producing organisms IR3 [ATCC 202150] and IR10 [ATCC 202151] according to standard protocols (Maniatis, supra) and compared with sequences in public databases. The comparison revealed that the 16s rRNA sequence most closely compared to that isolated from Burkholderia (97% identity), although there was significant identity to 16s rRNA from Pseudomonas.

Another distinguishing characteristic of the TPA producing organisms of the present invention is the presence of all of the enzymes of the TPA biosynthetic pathway. By the TPA biosynthetic pathway it is meant that all the enzymes, xylene monooygenase→methylbenzyl alcohol dehydrogenase→tolualdehyde dehydrogenase→toluate methyl monooxygenase→carboxybenzyl alcohol methyl dehydrogenase→caboxybenzaldehyde methyl dehydrogenase, are present and functionally linked in the order listed. The presence of a single organism comprising this complete cadre of linked enzymes is unique in the art.

Process for the Production of Terephthalic and Isophthalic Acids and Intermediates TPA producing microorganisms of the present invention may be used to produce both TPA and IPA. Additionally, a mixture of microorganisms may be cultured together for the production of TPA or IPA, where the microorganisms comprising the mixed culture, collectively, have all the enzymes of the TPA biosynthetic pathway.

Where the production of TPA is desired the TPA producing microorganism is contacted with p-xylene in a suitable growth medium and the reaction medium is monitored for the production of TPA. Where the production of IPA is desired it may be necessary to contact the TPA producing organism with a mixture of aromatic organic substrates to effect IPA production. For example the appropriate starting material for the production of IPA using the TPA biosynthetic enzymes is m-xylene. However, the TPA producers of the present invention are unable to use m-xylene as a sole carbon source. It is well known that bacteria sometimes metabolically transform a compound that can not be used for growth if a second compound is present that induces synthesis of the appropriate enzymes (Janke et al., *J. Basic Microbiol.* 25:603–619 (1985)). In the context of the present invention m-xylene was co-fed with p-xylene as an inducer to effect the conversion of m-xylene to IPA. Although p-xylene is a preferred inducer, it is contemplated that any of the intermediates converted or acted up by the enzymes of the TPA pathway in the production of TPA, including but not limited to p-xylene, 4-methylbenzyl alcohol, p-tolualdehyde, p-toluic acid, 4-carboxybenzyl alcohol, and 4-carboxybenzaldehyde will be effective inducers.

The present process is also usful for the production of any of the intermediates of the TPA biosynthetic pathway that may occur either in the bio-conversion of p-xylene to TPA or of m-xylene to IPA. For example, 4-carboxybenzyl alcohol is detected in cultures of isolate IR3 (ATCC 202150) that were given p-xylene as the sole source of carbon and energy. Thus, it is contemplated that any one of the intermediates involved in TPA production, such as 4-methylbenzyl alcohol, p-tolualdehyde, p-toluic acid, 4-carboxybenzyl alcohol, and 4-carboxybenzaldehyde for example, and the intermediates involved in IPA production, such as 3-methylbenzyl alcohol, m-tolualdehyde, m-toluic acid, 3-carboxybenzyl alcohol, and 3-carboxybenzaldehyde could be produced by the present TPA producing microorganisms.

These intermediates could be produced by using mutations to inactivate genes encoding key enzymes in the TPA biosynthetic pathway by. A mutation is a change in the nucleotide sequence of a gene. A variety of methods for introducing point mutations, insertion mutations or deletion mutations into specific genes are well known and have been described in the art (Maniatis supra). A mutation frequently inactivates or "knocks out" the protein product of the mutated gene. If a gene in a biosynthetic pathway is disrupted by a mutation, there may be accumulation of the pathway intermediate formed by the enzyme that catalyzes the synthetic step immediately prior to the step normally catalyzed by the enzyme knocked out by a mutation (Mengin-Lecreulx, D. and J. van Heijenoort, *J. Bacteriol.* 175: 6150–6157 (1993)). For example, a TPA producer could be used to develop a mutant bacterial strain that produces 4-methylbenzyl alcohol from p-xylene. The mutant strain would have a knockout mutation in the gene for the enzyme 4-methylbenzyl alcohol dehydrogenase to prevent conversion of 4-methylbenzyl alcohol to 4-methylbenzaldehyde. Under these conditions, a person skilled in the art would expect the mutant strain to accumulate 4-methylbenzyl alcohol because 4-methylbenzyl alcohol can not be converted to 4-methylbenzaldehyde by the mutant strain. Since 4-methylbenzyl alcohol will accumulate if the gene for 4-methylbenzyl alcohol dehydrogenase has a knockout mutation, the methyl group on 4-methylbenzyl alcohol would be available in unusually high amounts in the mutant as a possible substrate for xylene monooxygenase and/or toluate methyl monooxygenase. Accordingly, the mutant bacterial strain might also produce 1,4-benzenedimethanol as a result of the methyl group on 4-methylbenzyl alcohol being oxidized by xylene monooxygenase and/or toluate methyl monooxygenase. Similar considerations pertain to mutants that would accumulate 4-methylbenzaldehyde, terephthalaldehyde, or other intermediates of the TPA biosynthetic pathway.

One way to construct appropriate knockout mutations that would cause accumulation of a particular intermediate of the TPA biosynthetic pathway, e.g., 4-methylbenzyl alcohol, would initially involve inserting a functional antibiotic resistance gene sequence into a cloned copy of the 4-methylbenzyl alcohol dehydrogenase gene. The inserted antibiotic resistance gene would prevent the cloned 4-methylbenzyl alcohol dehydrogenase gene from being expressed. The 4-methylbenzyl alcohol dehydrogenase gene with inserted antibiotic resistance gene would be mobilized into the TPA producer on a plasmid vector that is unable to replicate in the TPA producer. Genetic selection for the inserted antibiotic resistance gene will yield recombinants in which the plasmid-borne 4-methylbenzyl alcohol dehydrogenase gene with inserted antibiotic resistance gene has replaced the original intact copy of the 4-methylbenzyl alcohol dehydrogenase gene. The result would be a new bacterial strain with a knockout mutation of the 4-methylbenzyl alcohol dehydrogenase gene which causes 4-methylbenzyl alcohol to accumulate. Appropriate antibiotic resistance gene sequences and plasmid vectors are well known in the art (Schweizer, H. P., et al., pages 229–237, in *Molecular Biology of Pseudomonads* (Nakazawa etal., eds.), ASM Press, Washington, D.C. (1996)).

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Techniques suitable for use in the following examples may be found in Sambrook, J., Fritsch, E. F. and Maniatis, T., *Molecular Cloning: A Laboratory Manual*, Second Edition, Cold Spring Harbor Laboratory Press, Cold Spring Harbor, N.Y. (1989) (hereinafter "Maniatis").

Materials and methods suitable for the maintenance and growth of bacterial cultures are well known in the art. Techniques suitable for use in the following examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994)); or by Thomas D. Brock in *Biotechnology: A Textbook of Industrial Microbiology*, Second Edition, Sinauer Associates, Inc., Sunderland, Mass. (1989). All reagents and materials used for the growth and maintenance of bacterial cells were obtained from Aldrich Chemicals (Milwaukee, Wis.), DIFCO Laboratories (Detroit, Mich.), GIBCO/BRL (Gaithersburg, Md.) or Sigma Chemical Company (St. Louis, Mo.) unless otherwise specified.

The meaning of abbreviations is as follows: "h" means hour(s), "min" means minute(s), "sec" means second(s), "d" means day(s), "μL" means microliter, "mL" means milliliters, "L" means liters, "μm" means micrometer, "ppm" means parts per million, i.e., milligrams per liter.

Media

Synthetic S12 medium was used to establish enrichment cultures and to culture bacteria for production of terephthalic acid. S12 medium contains the following: 10 mM ammonium sulfate, 50 mM potassium phosphate buffer (pH 7.0), 2 mM $MgCl_2$, 0.7 mM $CaCl_2$, 50 μM $MnCl_2$, 1 μM $FeCl_3$, 1 μM $ZnCl_3$, 1.72 μM $CuSO_4$, 2.53 μM $CoCl_2$, 2.42 μM $Na_2MoO_2$, 0.0001% $FeSO_4$ and 2 μM thiamine hydrochloride.

S12 agar was used to isolate bacteria from liquid enrichment cultures that grow on p-xylene and to test isolates for growth with p-xylene, p-toluic acid or terephthalic acid supplied a sole source of carbon and energy. S12 agar was prepared by adding 1.5% Noble agar (DIFCO) to S12 medium.

Bacteria growing in S12 medium were supplied with toluene, m-xylene or p-xylene as vapor by allowing the volatile compound to evaporate from a sterile 13×100 mm glass test tube reservoir inside of a glass screw cap culture flask. Bacteria growing on S12 agar were supplied with toluene, m-xylene, p-xylene or other volatile compounds as vapor by placing 5 μL of a volatile compound on the interior of the petri dish lid. The petri dish was sealed with parafilm and incubated with the lid on the bottom.

Stock solutions of terephthalic acid (Amoco refined 99.9%) and p-toluic acid (Aldrich) were prepared in 1N NaOH.

Isolation and Identification of Terephthalic Acid and Isophthalic Acid

The conversion of m-xylene and p-xylene to isophthalic acid and terephthalic acid, respectively, was monitored by reverse phase HPLC. Culture supernatants were passed through 0.2 μm filters (Gelman acrodisc CR PFTE or Millipore millex-gs) prior to analysis. Analyses were performed on either a Hewlett Packard HPLC model 1050 equipped with a Milton Roy LDC single wavelength detector set at 214 nm or a Hewlett Packard HPLC model 1090 equipped with a diode array UV-visible detector set at 254 nm (primary wavelength), 230 nm (secondary wavelength), and 450 nm as background reference. Samples (10 μL) were injected onto a Zorbax C8 column (2.1 mm×15 cm). The mobile phase consisted of (A) $H_2O$ containing 2 mL phosphoric acid/L and (B) acetonitrile. Gradients were as follow: a) 0 minutes to 25 minutes (B) increased from 10% to 25%, b) (B) increased to 95% over the next 12 minutes, c) (B) was held at 95% for 3 minutes, and d) (B) decreased to 10% in 1 min. Standards for HPLC were DHBA (dihydroxybenzoic acid), TMA (trimalinic acid), PA (phthalic acid), TPA (terephthalic acid), IPA (isophthalic acid), 4-CBAL (4-carboxybenzyl alcohol), 4-CBA (4-carboxybenzaldehyde), BA (benzoic acid), 4-MBAL (4-methylbenzaldehyde), MHT, PTA (p-toluic acid), PTL (p-tolualdehyde) and p-xylene in 96% tetrahydrofuran and 4% millipore water. All calibrations and data analysis was done using Hewlett Packard's Chemstation Software. Preparative HPLC for peak collection was run on instrument II with either a Zorbax RXC8 9.4 mm×25 cm with a 50–250 μL injection volume. The mobile phase consisted of (A) $H_2O$ containing 2 mL phosphoric acid/L or 2 mL acetic acid and (B) acetonitrile. For peak collection, samples were run in 2 mL acetic acid/1L of Milli-Q water mobile phase. Peaks of interest were collected into 20 mL glass vials. Samples were then subsequently concentrated in a Savant Speed Vac.

Example 1

Isolation and Identification of Bacteria That Grow With p-Xylene, p-Toluic Acid and Terephthalic Acid as Sole Sources of Carbon and Energy Various bacteria were isolated that could grow on p-xylene as the sole source of carbon and energy. Several of these isolates also grew on p-toluic acid and terephthalic acid supplied individually as sole sources of carbon and energy. Since p-toluic acid is an expected intermediate in the metabolic oxidation of p-xylene to terephthalic acid by bacteria, a collection of isolates that grow on p-xylene, p-toluic acid and terephthalic acid is likely to include bacteria that enzymatically oxidize p-xylene to terephthalic acid. Analysis of 16s rRNA gene sequences indicated that the collection of isolates included members of the bacterial genra Pseudomonas and Burkholderia.

Bacteria that grow on p-xylene, p-toluic acid and terephthalic acid were isolated from an enrichment culture. The enrichment culture was established by inoculating 1 mL of activated sludge into 10 mL of S12 medium in a 125 mL screw-cap Erlenmeyer flask. The activated sludge was obtained from a wastewater treatment facility. The enrichment culture was supplemented with 100 ppm p-xylene added directly to the culture medium and was incubated at 25° C. with reciprocal shaking. The enrichment culture was maintained by adding 100 ppm p-xylene every 2–3 days. The culture was diluted every 10 days by replacing 9 mL of the culture with the same volume of S12 medium. After 29 days of incubation, serial dilutions of the enrichment culture were spread onto R2A agar (DIFCO) and S12 agar. p-Xylene was placed on the interior of each petri dish lid. The petri dishes were sealed with parafilm and incubated upside down at room temperature (25° C.).

Representative bacterial colonies were then tested for the ability to use p-xylene as a sole source of carbon and energy. Colonies were transferred from the R2A plates and S12 agar plates to the S12 agar plates and supplied with p-xylene as vapor by placing 5 μL of p-xylene on the interior of each petri dish lid. The petri dishes were sealed with parafilm and incubated upside down at room temperature (25° C.). The isolates that utilized p-xylene for growth were then tested for growth on S12 agar plates containing either p-toluic acid (6 mM) or terephthalic acid (100 μg/mL).

The 16s rRNA genes of each isolate were amplified by PCR and analyzed as follows. Each isolate was grown on R2A agar. Several colonies from each culture plate were suspended in 200 mL of lysis buffer (1% Triton X-100, 20 mM Tris (pH 8.5), 2 mM EDTA). The mixture was heated to 95° C. for 10 min and then centrifuged to remove cellular debris. The 16s rRNA gene sequences in the supernatant were amplified by PCR by using a commercial kit according to the manufacturer's instructions (Perkin Elmer) with HK12 primer GAG TTT GAT CCT GGC TCA G (SEQ ID NO:2) and HK13 primer TAC CTT GTT ACG ACT T (SEQ ID NO:3). PCR was performed in a Perkin Elmer GeneAMp 9600. The samples were incubated for 5 min at 94° C. and then cycled 35 times at 94° C. for 30 sec, 55° C. for 1 min and 72° C. for 1 min. The amplified 16s rRNA genes were purified using a commercial kit according to the manufacturer's instructions (QIAquick PCR Purification Kit) and sequenced on an automated ABI sequencer. The sequencing reactions were initiated with HK12 primer, HK13 primer and HK14 primer GTG CCA GCA GYM GCG GT; Y=C or T, M=A or C (SEQ ID NO:4). The 16s rRNA gene sequence of each isolate was used as the query sequence for a FastA search (Wisconsin Package Version 9.0, Genetics Computer Group (GCG), Madison, Wis.) of GenBank for similar sequences.

The data in Table 1 indicated that 6 out of 20 isolates from the p-xylene enrichment culture were able to grow on p-xylene, p-toluic acid and terephthalic acid as sole sources of carbon and energy. The 16s rRNA genes of these six isolates were sequenced and compared to other 16s rRNA sequences in the GenBank sequence database. The 16s rRNA genes from isolates DSK1 and DS6 had high degrees of homology with bacterial species belonging to the genus Pseudomonas, whereas isolates IR3 (ATCC 202150), IR10 (ATCC 202151) and IS3 had a high degree of homology with the genus Burkholderia (Table 2). Comparison of the 16s rRNA gene sequence of IR3 (ATCC 202150) (SEQ ID NO:1) to the 16s rRNA gene sequence, IR10 (ATCC 202151) and IS3 indicated that the 16s rRNA genes of these isolates were at least 98% homologous (Table 2).

TABLE 1

Summary of Carbon Source Utilization

| | Growth on Carbon Source | | |
|---|---|---|---|
| Isolate | p-Xylene | p-Toluic Acid | Terephthalic Acid |
| DR3 | +/− | − | + |
| DR7 | + | + | − |
| DR9 | + | + | − |
| DR11 | + | + | − |
| DR13 | + | − | +/− |
| DSK1 | + | + | + |
| DSK2 | +/− | − | + |
| DS2 | + | + | − |
| DS3 | + | + | − |
| DS6 | + | + | + |
| DS7 | + | + | − |
| IR1 | + | − | + |
| IR3 | + | + | + |
| IR4 | + | + | + |
| IR10 | + | + | + |
| IS2 | − | + | +/− |
| IS3 | + | + | + |
| IS4 | +/− | + | − |
| IS6 | + | + | − |
| IS8 | + | + | − |

TABLE 2

Comparison of 16s rRNA genes

| Isolate | Closest Match | % homology to closest match | % homology to IR3 |
|---|---|---|---|
| DSK1 | Pseudomonas graminis | 97.6 | 84.3 |
| DS6 | Pseudomonas testosteroni | 94.1 | 89.0 |
| IR3 | Burkholderia sp. | 97.6 | 100 |
| IR10 | Burkholderia sp. | 97.8 | 99.3 |
| IS3 | Burkholderia sp. | 97.2 | 98.3 |

Example 2

Conversion of p-Xylene Into Terephthalic Acid by Bacteria of the Genus Burkholderia Example 2 demonstrated that strain IR3 (ATCC 202150) and other Burkholderia isolates produced terephthalic acid when grown in S12 medium with p-xylene supplied as the only source of carbon and energy. Since all of the Burkholderia isolates had a high degree of homology in the 16s rRNA genes and preliminary experiments indicated that all four isolates produced terephthalic acid, isolate IR3 (ATCC 202150) was selected for further characterization. Isolate IR3 was grown to an optical density at 600 nm ($OD_{600}$) of 0.968 in 60 mL of S12 medium in a 250 mL screw-cap Erlenmeyer flask with 500 μL of p-xylene in a reservoir. The cells were harvested by centrifugation and resuspended in S12 medium at an $OD_{600}$ of 0.654. The cells were divided into three 35 mL aliquots. Each aliquot was dispensed into a sterile 125 mL screw-cap Erlenmeyer flask. One flask was autoclaved with its contents for 15 min (killed cell control). The cells in the autoclaved flask were exposed to vapor from 500 μL of p-xylene in a reservoir. The cells in the second flask were exposed to vapor from 500 μL of p-xylene in a reservoir. The cells in the third flask were not exposed to p-xylene. A fourth flask containing S12 medium exposed to vapor from 500 μL of p-xylene in a reservoir was established as a control to demonstrate that the culture medium alone did not convert p-xylene to terephthalic acid. All of the flasks were incubated at 30° C. with reciprocal shaking. Samples (1.5 mL) were collected at the indicated times and passed through 0.22 μm Acrodisc CR PFTE filters. The first sample was collected immediately after the cells were suspended in new medium (0 h). The samples were analyzed by HPLC. Terephthalic acid and p-toluic acid were identified by retention times.

The data in Table 3 indicated that p-toluic acid and terephthalic acid could be detected in a culture of IR3 (ATCC 202150) after 9 h of incubation when viable cells were exposed to p-xylene vapor. p-Xylene was necessary for production of p-toluic acid and terephthalic acid since neither compound was detected when viable cells were incubated without p-xylene. Furthermore, viable cells were necessary for production of p-toluic acid and terephthalic acid, since neither compound was detected when autoclaved cells or medium alone were incubated with p-xylene. Similar experiments demonstrated that isolates IR4, IR10 (ATCC 202151) and IS3 all produced significant amounts of terephthalic acid when cultured with p-xylene, whereas isolates DSK1 and DS6 did not produce detectable amounts of terephthalic acid when cultured with p-xylene.

TABLE 3

Production of p-toluic acid and terephthalic acid from p-xylene by Burkholderia strain IR3 (ATCC 202150)

| | | Concentration (ppm) | |
|---|---|---|---|
| Time (h) | Culture | PTA | TPA |
| 0 | cells alone | ND[a] | ND |
| | killed cells + p-xylene | ND | ND |
| | cells + p-xylene | ND | ND |
| | medium + p-xylene | ND | ND |
| 9 | cells alone | ND | ND |
| | killed cells + p-xylene | ND | ND |
| | cells + p-xylene | 0.76 | 0.40 |
| | medium + p-xylene | ND | ND |

[a]Not detected

Example 3

Analysis of Terephthalic Acid Produced by Bacteria of the Genus Burkholderia

Example 3 demonstrated that the p-toluic acid, 4-carboxybenzyl alcohol and terephthalic acid produced from p-xylene by Burkholderia IR3 (ATCC 202150) were identical to authentic standards by HPLC diode array analysis and mass spectrometry. These results support the conclusion that isolate IR3 (ATCC 202150) produces terephthalic acid from p-xylene by means of a previously unknown pathway.

HPLC Diode Array Analysis

Isolate IR3 (ATCC 202150) was grown to an $OD_{600}$ of 0.60 in 20 mL of S12 medium in a 250 mL screw-cap Erlenmeyer flask with 200 μL of p-xylene in a reservoir. Samples (1.5 mL) of the culture were placed in 1.5 mL microfuge tubes and mixed with 15 μL of p-xylene. The samples were incubated without shaking for 72 hours at 25° C. and then filtered. The samples were analyzed by reverse-phase HPLC with a diode array UV-visible detector set at 240 nm.

The chromatogram in FIG. 1 indicated that three major compounds were present in the IR3 culture. The compounds were presumptively identified by comparison of HPLC retention times with authentic standards (Table 4). The UV absorbance spectra of authentic 4-carboxybenzyl alcohol, terephthalic acid and p-toluic acid standards were compared to the UV spectra of the presumptive 4-carboxybenzyl alcohol, terephthalic acid and p-toluic acid peaks (FIGS. 2A and 2B, 3A and 3B, and 4A and 4B, respectively). The UV-visible spectrum of each compound detected in the IR3 culture was identical to the UV-visible absorbance spectrum of the corresponding standard. These results supported two conclusions. First, each one of the three major peaks that were detected by HPLC represented a single compound. Second, comparison of the UV spectra confirmed the presumptive identification of each peak.

TABLE 4

Production of p-toluic acid and terephthalic acid from p-xylene by Burkholderia strain IR3 (ATCC 202150)

| Peak | Peak Retention Time (min) | Standard | Standard Retention Time (min) |
|---|---|---|---|
| 1 | 6.487 | 4CBA | 6.488 |
| 2 | 9.587 | TPA | 9.571, 9.568 |
| 3 | 24.188 | PTA | 24.173 |

Mass Spectrometry

Isolate IR3 (ATCC 202150) was grown to an $OD_{600}$ of 0.60 in duplicate 250 mL screw-cap Erlenmeyer flasks containing 23 mL of S12 medium with 200 μL of p-xylene in a reservoir. Aliquots (1.0 mL) of the cultures were placed in 1.5 mL microfuge tubes and mixed with 10 μL of p-xylene. The aliquots were incubated without shaking for 72 hours at 25° C. and then filtered. The aliquots from each flask were pooled and a 1 mL sample from each pool was analyzed by reverse-phase HPLC with a diode array UV-visible detector at 240 nm. Three major compounds were present in the IR3 cultures. The compounds were presumptively identified by retention times as 4-carboxybenzyl alcohol, terephthalic acid and p-toluic acid.

The filtered supernatants derived from both IR3 cultures were combined for preparative HPLC. Preparative HPLC was performed with a Zorbax RXC8 9.4 mm×25 cm (HP part no. 880952.206) with a 50–250 μL injection volume. The mobile phase consisted of (A) $H_2O$ containing 2 mL of acetic acid/L and (B) acetonitrile. The peaks corresponding to 4-carboxybenzyl alcohol, terephthalic acid and p-toluic acid were manually collected from the HPLC effluent into 20 mL glass vials. Each of the collected peaks was concentrated to approximately 1 mL in a Savant Speed Vac.

GC-MS was performed on a Hewlett Packard 5890 Series II GC with a HP 5971 Mass Selective Detector. The column was a HP-5 MS 30 m×0.25 mm with 0.25 μm film thickness. Samples of HPLC peaks and standards were dried and derivatized with 1 ampule of dimethylacetamide dimethyl acetal in a closed vial at 60° C. for 30 min, venting after 5 and 10 minutes. The vial was washed with a small amount of reagent-grade methanol, and the vial was incubated at 60° C. for an additional 20 min. Derivatized samples (2 μL) were injected, held at 40° C. for 1 min, ramped to 280° C. at a rate of 10 degrees per minute, and held at that temperature for 5 min. This analysis confirmed that isolate IR3 (ATCC 202150) produced p-toluic acid.

MS/MS was performed on a Finnigan SSQ 7000 mass spectrometer. Derivatized samples and standards were analyzed by direct insertion with a probe into the mass spectrometer in electron impact mode using a single quadrapole. The probe was ramped from 40° C. to 300° C. at 26 degrees per min. This analysis confirmed that isolate IR3 (ATCC 202150) produced p-toluic acid and terephthalic acid.

Mass spectrometry analysis was performed on a TSQ700 mass spectrometer from Finnigan of San Jose, Calif. The ion source was electrospray with a heated capillary (Finnigan). The pooled and concentrated HPLC peaks of p-toluic acid, 4-carboxybenzyl alcohol and terephthalic acid were diluted 1:1 in acetonitrile. The samples were directly infused into the instrument which was run in electrospray negative ion mode (single quadrapole). The scanning range was 50 to 350. This analysis confirmed that isolate IR3 (ATCC 202150) produced p-toluic acid, 4-carboxybenzyl alcohol and terephthalic acid.

Figure 5:
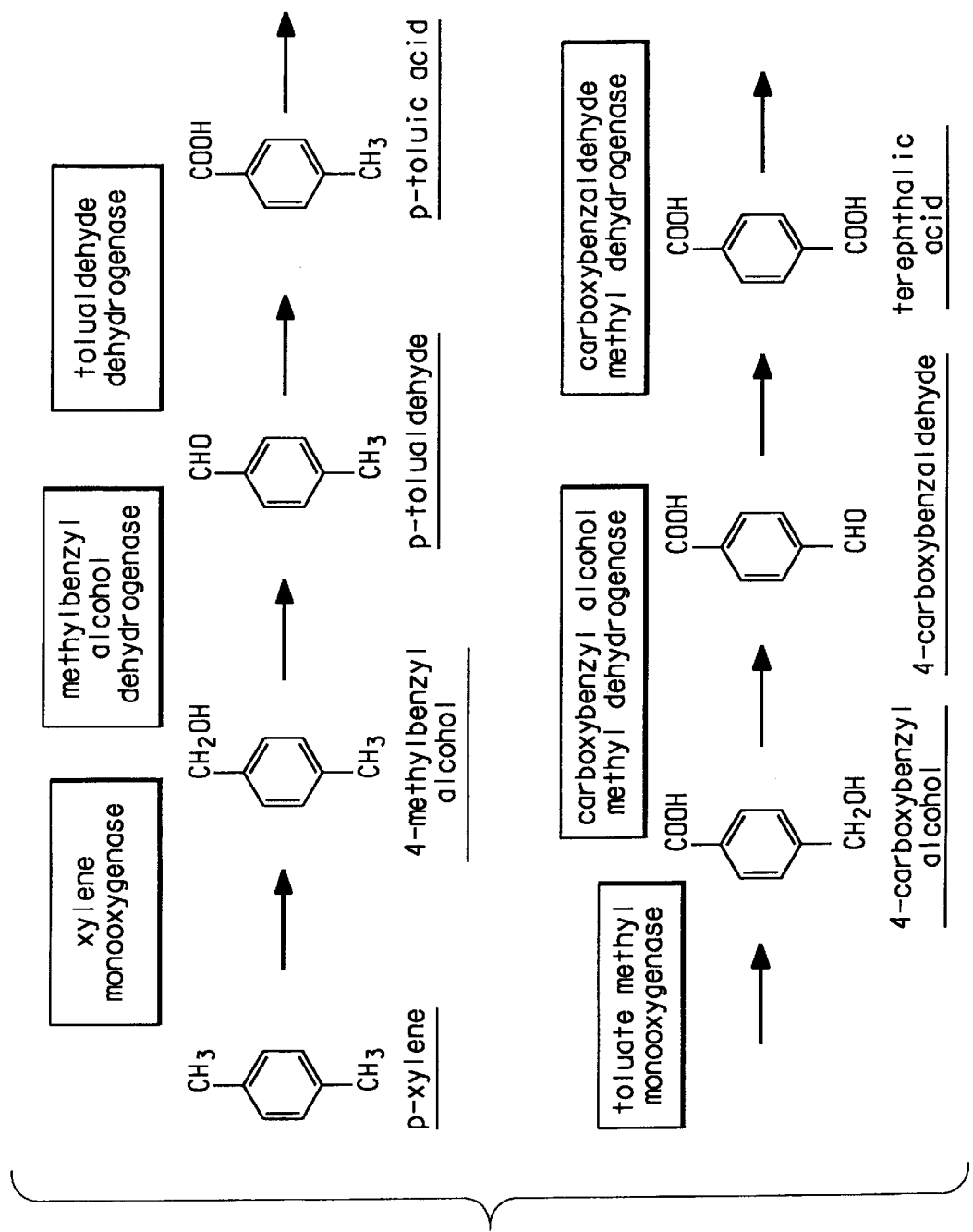
FIG. 5 shows the synthesis path of terephthalic acid from p-xylene by Burkholderia isolate IR3.

Metabolic Pathway for Conversion of p-xylene Into Terephthalic Acid p-Toluic acid, 4-carboxybenzyl alcohol and terephthalic acid were detected in cultures of isolate IR3 (ATCC 202150) that were given p-xylene as the sole source of carbon and energy. This result was consistent with sequential oxidation of one methyl group on p-xylene to form p-toluic acid with subsequent sequential oxidation of the second methyl group to form terephthalic acid (FIG. 5). Although 4-methylbenzyl alcohol, 4-methylbenzaldehyde and 4-carboxybenzaldehyde were not detected in cultures of isolate IR3 (ATCC 202150), IR3 utilized all three of these compounds as sole sources of carbon and energy.

Example 4

Production of Terephthalic Acid From p-Xylene by Isolate IR10 (ATCC 202151) After Growth in Rich Medium Example 4 demonstrates that Burkholderia isolate IR10 (ATCC 202151) converted p-xylene to terephthalic acid after initial growth in LB medium indicating that one type of medium could be used to generate cell mass and that the cells could be switched to a second medium for production of terephthalic acid. Isolate IR10 (ATCC 202151) was grown for 9 h in 45 mL of LB medium in a 250 mL screw-cap Erlenmeyer flask with 250 μL of p-xylene in a reservoir. The flask was incubated at 28° C. with shaking. The cells were harvested by centrifugation and resuspended in 40 mL of S12 medium. A 20 mL aliquot of cells was incubated at 25° C. without shaking for 30 min in a 250 mL screw-cap Erlenmeyer flask with 200 μL of p-xylene in a reservoir. Samples (1.5 mL) were removed from the flask and mixed with 15 μL of p-xylene in a microfuge tube. The samples were incubated at 25° C. without shaking for the times indicated in Table 5. The samples were filtered and analyzed for p-toluic acid and terephthalic acid by HPLC. P-Toluic acid and terephthalic acid were identified by retention times.

The data in Table 5 indicate that cells initially grown in LB medium and resuspended in S12 medium produced significant amounts of p-toluic acid and terephthalic acid during a short incubation. The amounts of p-toluic acid and terephthalic acid increased with prolonged incubation.

TABLE 5

Production of p-toluic acid and terephthalic acid after growth in LB medium

| Incubation Time | Concentration (ppm) | |
|---|---|---|
|  | PTA | TPA |
| 30 min | 137.1 | 24.7 |
| 3 days | 886.3 | 89.0 |

Example 5

Production of Isophthalic Acid from m-Xylene by Isolate IR3

Figure 6:
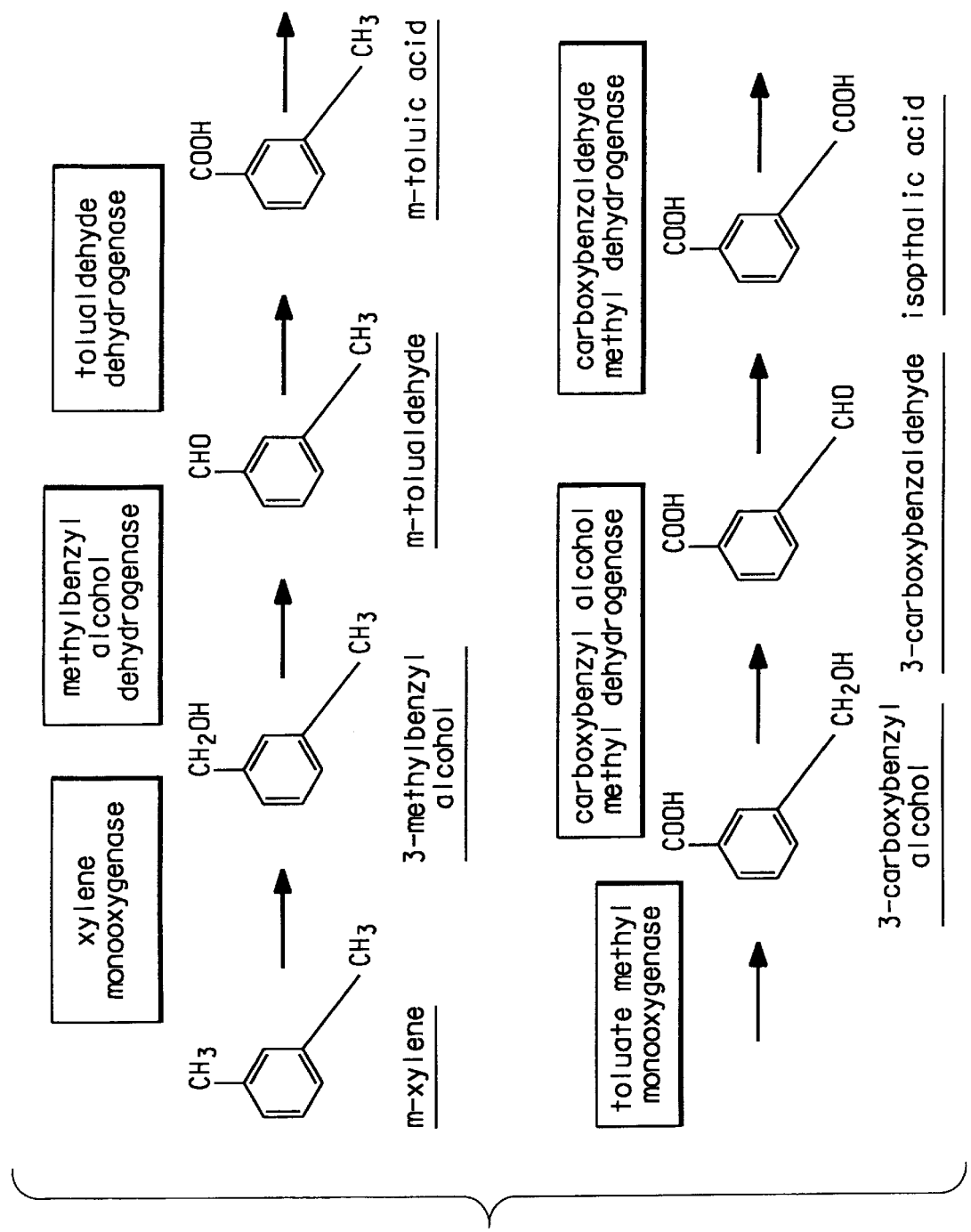
FIG. 6 shows the synthesis path of isophthalic acid from m-xylene by Burkholderia isolate IR3.

Example 5 demonstrates that isolate IR3 converted m-xylene into m-toluic acid and isophthalic acid in the presence of p-xylene. The conversion follows the pathway as outlined in FIG. 6.

Isolate IR3 was grown for 18 h in 25 mL of S12 medium in 250 mL screw-cap Erlenmeyer flasks with 200 µL of p-xylene or a mixture of 100 µL of p-xylene and 100 µL of m-xylene in a reservoir. The cultures were diluted to an $OD_{600}$ of 0.30 and 25 mL aliquots were dispensed into screw-cap Erlenmeyer flasks. The culture that had been grown with p-xylene alone was given a reservoir with 200 µL of p-xylene. The culture that had been grown with p-xylene and m-xylene was given a reservoir with a mixture of 100 µL of p-xylene and 100 µL of m-xylene. The cultures were incubated without shaking at 28° C. Samples (1.5 mL) were collected at the indicated times and filtered. The first sample was collected immediately after the cells were suspended in new medium (0 h). The samples were analyzed by HPLC and p-toluic acid, terephthalic acid, m-toluic acid and isophthalic acid were identified by retention times.

The data in Table 4 indicate that bacteria initially grown and then incubated with p-xylene alone produced p-toluic acid and terephthalic acid. Isophthalic acid was not detected in the p-xylene culture. A small amount of m-toluic acid was in the culture at the end of the experiment. Production of m-toluic acid in this culture was attributed to the presence of a residual amount of m-xylene (<1%) in the commercial stock of p-xylene. Bacteria initially grown and then incubated with a mixture of p-xylene and m-xylene also produced small amounts of p-toluic acid and terephthalic acid. The bacteria exposed to p-xylene and m-xylene produced high levels of m-toluic acid after the initial sample time. A significant level of isophthalic acid was detected in the culture after 278 h. The UV-visible absorbance spectra of the presumptive m-toluic acid and isophthalic acid peaks were compared to the UV-visible spectra of authentic standards. The UV-visible spectra of m-toluic acid and isophthalic acid detected in the IR3 culture were identical to the UV-visible absorbance spectrum of the corresponding standards. These results supported two conclusions. First, the presumptive m-toluic acid and isophthalic acid HPLC peaks represented single compounds. Second, comparison of UV-visible spectra confirmed the presumptive identification of each peak. Therefore, isolate IR3 (ATCC 202150) converted m-xylene into m-toluic acid and isophthalic acid in the presence of p-xylene even though m-xylene alone could not be utilized for growth.

TABLE 5

Production of m-toluic acid and isophthalic acid from m-xylene by Burkholderia strain IR3 (ATCC 202150)

| Time (h) | Carbon Source | Concentration (ppm) | | | |
|---|---|---|---|---|---|
|  |  | PTA | TPA | MTA | IPA |
| 0 | p-xylene | ND[a] | ND | ND | ND |
|  | p-xylene + m-xylene | ND | ND | ND | ND |
| 69 | p-xylene | 231.8 | ND | ND | ND |
|  | p-xylene + m-xylene | 6.4 | 5.3 | 490.5 | ND |
| 116 | p-xylene | 577.0 | 24.2 | ND | ND |
|  | p-xylene + m-xylene | ND | 56.0 | 661.1 | ND |
| 278 | p-xylene | 308.8 | 104.4 | 2.5 | ND |
|  | p-xylene + m-xylene | ND | ND | 833.1 | 12.3 |

[a]Not detected

Example 6

Production of Terephthalic Acid from p-Xylene in Mixed Cultures of *Pseudomonas putida* Strain ATCC 33015 and *Comamonas testosteroni* Strain DSM 6577

Biological production of terephthalic acid from p-xylene requires a set of enzymes that oxidize both methyl groups of p-xylene. Conversion of p-xylene into terephthalic acid by isolate IR3 is accomplished by a single cell line or single bacterial strain that produces all of the requisite enzymes. Example 6 demonstrates that a bacterial strain that converts p-xylene into p-toluic acid (strain ATCC 33015) could be mixed with a different bacterial strain that converts p-toluic acid into terephthalic acid (DSM 6577) with the result that the mixture of bacteria converted p-xylene into TPA.

Strain ATCC 33015 was grown for 18 h in 25 mL of S12 medium in a 250 mL screw-cap Erlenmeyer flask with 100 µL of p-xylene in a reservoir. The cells were harvested by centrifugation and resuspended in 15 mL of S12 medium. Strain DSM 6577 was grown 6 h in 25 mL of LB medium in a 250 mL screw-cap Erlenmeyer flask. The DSM 6577 cells were harvested by centrifugation and resuspended in 50 mL of S12 medium. One control flask had ATCC 33015 alone in 25 mL of S12 medium at an initial $OD_{600}$ of 0.05. A second control flask had DSM 6577 alone in 25 mL of S12 medium at an initial $OD_{600}$ of 0.01. A third flask was inoculated with 3 mL ATCC 33015 cells and 1 µmL of the DSM 6577 cells. Each flask had a reservoir with 200 µL of p-xylene. The cultures were incubated without shaking at 28° C. Samples (1.5 mL) were collected at the indicated times and filtered. The first sample was collected immediately after the two types of bacteria were mixed (0 h). The samples were analyzed by HPLC and 4-carboxybenzyl alcohol, p-toluic acid and terephthalic acid were identified by retention times.

TABLE 6

Production of terephthalic acid from p-xylene in mixed cultures of ATCC 33015 and DSM 6577

| Time (h) | Culture | Concentration (ppm) | | |
|---|---|---|---|---|
|  |  | PTA | 4CBAL | TPA |
| 0 | ATCC 33015 | ND[a] | ND | ND |
|  | DSM 6577 | ND | ND | ND |
|  | ATCC 33015 + DSM 6577 | ND | ND | ND |

TABLE 6-continued

Production of terephthalic acid from p-xylene in mixed cultures of ATCC 33015 and DSM 6577

| | | Concentration (ppm) | | |
|---|---|---|---|---|
| Time (h) | Culture | PTA | 4CBAL | TPA |
| 22 | ATCC 33015 | 89.6 | ND | ND |
| | DSM 6577 | ND | ND | ND |
| | ATCC 33015 + DSM 6577 | 150.4 | 1.4 | ND |
| 68 | ATCC 33015 | 20.4 | ND | ND |
| | DSM 6577 | ND | ND | ND |
| | ATCC 33015 + DSM 6577 | 226.8 | 1.6 | 0.08 |

[a]Not detected

What is claimed is:

1. A process for the production of terephthalic acid comprising:
   (i) contacting an isolated TPA producing Proteobacteria with an aromatic organic substrate selected from the group consisting of p-xylene, 4-methylbenzyl alcohol, and p-tolualdehyde, whereby terephthalic acid is produced; and
   (ii) recovering the terephthalic acid.

2. The process of claim 1 wherein the TPA producing microorganism is isolated by a process comprising:
   (i) culturing a sample suspected of containing a TPA producing microorganism in a suitable growth medium containing at least one aromatic organic substrate selected from the group consisting of p-xylene, p-toluic acid, and terephthalic acid;
   (ii) selecting those microorganisms which are able to use every substrate selected individually from the group consisting of p-xylene, p-toluic acid, and terephthalic acid as a sole carbon source;
   (iii) contacting the microorganisms selected in step (ii) with p-xylene to form a reaction medium; and
   (iv) monitoring the reaction medium over time for the presence of terephthalic acid, whereby the production of terephthalic acid indicates the presence of a TPA producing microorganism.

3. The process of claim 1 wherein the isolated TPA producing Proteobacteria is selected from the group consisting of, Burkholderia, Alcaligenes, Pseudomonas, Sphingomonas and Comamonas.

4. The process of claim 3 wherein the 16s RNA of the TPA producing microorganism has at least 97% identity with the 16s rRNA sequence set forth in SEQ ID NO:1.

5. The process of claim 1 wherein the isolated TPA producing microorganism is Burkholderia sp. selected from the group consisting of IR3 (ATCC 202150) and IR10 (ATCC 202151).

* * * * *